US009456763B2

(12) United States Patent
Gordon et al.

(10) Patent No.: US 9,456,763 B2
(45) Date of Patent: Oct. 4, 2016

(54) APPARATUS AND METHOD FOR SIMULTANEOUS CAPTURE OF BIOPOTENTIAL AND TISSUE IMPEDANCE SIGNALS

(71) Applicant: Medtronic, Inc., Minneapolis, MN (US)

(72) Inventors: Charles R. Gordon, Phoenix, AZ (US); Gregg T. Sarkinen, Montrose, MN (US); Michael B. Terry, Camas, WA (US)

(73) Assignee: Medtronic, Inc., Minneapolis, MN (US)

( * ) Notice: Subject to any disclaimer, the term of this patent is extended or adjusted under 35 U.S.C. 154(b) by 198 days.

(21) Appl. No.: 14/219,040

(22) Filed: Mar. 19, 2014

(65) Prior Publication Data

US 2015/0073295 A1    Mar. 12, 2015

Related U.S. Application Data

(60) Provisional application No. 61/876,440, filed on Sep. 11, 2013.

(51) Int. Cl.
| A61B 5/053 | (2006.01) |
| A61B 5/042 | (2006.01) |
| A61B 5/0428 | (2006.01) |
| A61B 5/04 | (2006.01) |
| A61B 5/0476 | (2006.01) |
| A61B 5/0488 | (2006.01) |

(52) U.S. Cl.
CPC ............... *A61B 5/053* (2013.01); *A61B 5/042* (2013.01); *A61B 5/0428* (2013.01); *A61B 5/0538* (2013.01); *A61B 5/04004* (2013.01); *A61B 5/0476* (2013.01); *A61B 5/0488* (2013.01)

(58) Field of Classification Search
CPC ....................................................... A61B 5/053
USPC ........................................................... 600/547
See application file for complete search history.

(56) References Cited

U.S. PATENT DOCUMENTS

| 5,309,917 | A | 5/1994 | Wang |
| 5,735,883 | A | 4/1998 | Paul |
| 5,957,861 | A | 9/1999 | Combs |
| 6,076,015 | A * | 6/2000 | Hartley ............. A61N 1/36521 600/547 |
| 6,882,166 | B2 * | 4/2005 | Shambroom ........ A61B 5/0531 324/692 |
| 7,622,988 | B2 | 11/2009 | Denison |
| 7,917,204 | B2 * | 3/2011 | Olson .................... A61B 5/053 600/547 |
| 8,452,557 | B2 * | 5/2013 | Naumann ............. G01R 27/26 324/627 |
| 8,454,505 | B2 | 6/2013 | Yazicioglu |
| 2006/0100539 | A1 * | 5/2006 | Min ..................... A61B 5/053 600/547 |

(Continued)

FOREIGN PATENT DOCUMENTS

| WO | 99/39636 | 8/1999 |
| WO | 2005122889 A1 | 12/2005 |

OTHER PUBLICATIONS (PCT/US2014/054662) PCT Notification of Transmittal of the International Search Report and the Written Opinion of the International Searching Authority.

*Primary Examiner* — Michael C Stout
(74) *Attorney, Agent, or Firm* — Evans M. Mburu

(57) ABSTRACT

A medical device and associated method acquire a biopotential signal from a pair of electrodes at a first sampling rate and a bioimpedance signal from the pair of electrodes at a second sampling rate. An onset and/or offset of the drive signal delivered to the pair of electrodes for acquiring the bioimpedance signal is synchronized to the first sampling rate.

26 Claims, 7 Drawing Sheets

(56) References Cited

U.S. PATENT DOCUMENTS

| | | | |
|---|---|---|---|
| 2008/0300504 A1* | 12/2008 | Lefkov | A61B 5/053 600/547 |
| 2009/0079606 A1 | 3/2009 | Terry et al. | |
| 2009/0156908 A1* | 6/2009 | Belalcazar | A61B 5/0031 600/301 |
| 2009/0326387 A1 | 12/2009 | Belalcazar et al. | |
| 2009/0326408 A1 | 12/2009 | Moon | |
| 2010/0113962 A1 | 5/2010 | Hettrick | |
| 2010/0324404 A1 | 12/2010 | Harrold et al. | |
| 2011/0066054 A1* | 3/2011 | Yazicioglu | A61B 5/04 600/509 |
| 2011/0092834 A1* | 4/2011 | Yazicioglu | A61B 5/0402 600/509 |

* cited by examiner

APPARATUS AND METHOD FOR SIMULTANEOUS CAPTURE OF BIOPOTENTIAL AND TISSUE IMPEDANCE SIGNALS

CROSS-REFERENCE TO RELATED APPLICATION

This application claims priority to provisional U.S. Application No. 61/876,440, filed Sep. 11, 2013, which is incorporated herein by reference in its entirety.

TECHNICAL FIELD

The disclosure relates generally to an implantable medical device (IMD) configured to acquire a bioimpedance signal and a biopotential signal concurrently using a common pair of electrodes.

BACKGROUND

Numerous implantable medical devices are available for acute or chronic implantation within patients. Some implantable medical devices may be used to chronically monitor physiological signals of the patient, such as implantable hemodynamic monitors, implantable cardiac monitors (sometimes referred to as implantable loop recorders or ECG monitors), implantable blood chemistry monitors, implantable pressure monitors, or the like. Other implantable devices may be configured to deliver a therapy in conjunction with or separate from the monitoring of physiological signals.

For example, in some medical applications, it may be advantageous to acquire both biopotential signals, such as intracardiac electrogram (EGM) signals, electrocardiography (ECG) signals, electromyogram (EMG) signals, or electroencephalogram (EEG) signals, to monitor electrical activity of a tissue or organ as well as bioimpedance signals, which may be correlated to a volume, pressure, fluid status or other characteristic of the monitored tissue or organ. In order to measure bioimpedance, an excitation or drive signal is applied to an electrode pair such that the resulting impedance between the electrodes can be determined, e.g. based on a voltage signal measured across the electrode pair after applying a drive current signal. The drive signal, if applied to the same pair of electrodes used for acquiring a biopotential signal, however, can produce significant noise and artifact on the biopotential signal. Typically, therefore, a biopotential signal and a bioimpedance signal are monitored using two different electrode pairs to avoid interference between the drive signal and the recorded biopotential signal. The requirement of two separate electrode pairs and corresponding feedthroughs through the device housing, however, increases the required size and volume of an implantable device and is contrary to the goal of reducing device size.

Advances in medical device technology have enabled implantable devices to be made smaller in size, which facilitates minimally invasive procedures for implanting the device and promotes patient comfort. Reduction of device size poses limitations on the space available for batteries, sensors, processing and control circuitry and other device components that support the primary device function. It is desirable, therefore, in a device that is used for monitoring both a bioimpedance signal and a biopotential signal, to eliminate the requirement of two electrode pairs for separately monitoring bioimpedance and biopotential signals.

DETAILED DESCRIPTION

Figure 1:
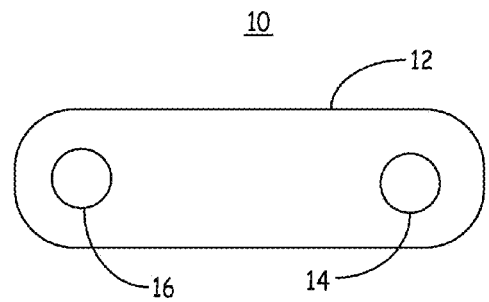
FIG. 1 is a conceptual diagram of an example IMD.

FIG. 1 is a conceptual diagram of an example IMD 10. IMD 10 is shown embodied as a monitoring device having a proximal electrode 14 and a distal electrode 16 located along an IMD housing 12. IMD housing 12 encloses electronic circuitry inside IMD 10 and protects the IMD circuitry from body fluids. Electrical feedthroughs provide electrical connection of electrodes 14 and 16 across IMD housing 12 to internal circuitry when electrodes 14 and 16 are positioned along the exterior surface of housing 12.

IMD 10 may be embodied as an implantable cardiac monitor wherein electrodes 14 and 16 are used to sense biopotential signals, e.g. ECG signals, intra-thoracically or extra-thoracically, which may be sub-muscularly or subcutaneously. ECG signals may be stored in memory of IMD 10, and ECG data may be transmitted by IMD 10 to another medical device, which may be another implantable device or an external device. In alternative applications, electrodes 14 and 16 may be used for sensing any biopotential signal of interest, which may be, for example, an EGM, EEG, EMG, or a nerve signal, from any implanted location.

IMD 10 is further configured to use electrodes 14 and 16 for measuring bioimpedance across electrodes 14 and 16 when implanted in a patient's body. The bioimpedance is the impedance of the body tissue and/or fluid present in a measurement volume adjacent to electrodes 14 and 16. The bioimpedance may be used for monitoring volume, pressure, fluid status, or other tissue or fluid changes that cause a change in impedance between electrodes 14 and 16.

Electrodes 14 and 16 may be formed of a biocompatible conductive material, e.g. titanium, platinum, iridium, or alloys thereof. The configuration illustrated in FIG. 1 is just one example electrode configuration. In other instances, sensing electrodes 14 and 16 may be located at other positions along IMD housing 12 than the positions shown in FIG. 1. For example, the electrodes 14 and 16 are shown both positioned along a top side of IMD 10, but in other examples electrodes 14 and 16 may be located on the bottom side or lateral side of IMD 10, on opposing sides of IMD 10, or on one or both ends of IMD 10. Additionally, all or a portion of housing 12 may function as one of the electrodes and be insulated from any other electrodes positioned along housing 12. An exemplary description of such a configuration is disclosed in commonly assigned and co-pending U.S. patent application Ser. No. 14/060,649, titled "Supply Noise Rejection In Implantable Medical Devices" (Reinke et al.), incorporated herein by reference in its entirety. In still other embodiments, an IMD system may include one or more electrodes carried by an electrical lead or tether extending away from the IMD and coupled to the IMD internal circuitry via electrical feedthroughs and conductors. In further instances, IMD 10 may include more than two electrodes for various monitoring or therapy delivery purposes, but a single pair of electrodes is used for both delivering a drive signal for measuring a tissue bioimpedance and for receiving a biopotential signal. The bioimpedance signal is also received from the same pair of electrodes. In other examples, the bioimpedance signal may be sensed from a different pair of recording electrodes than the single pair of electrodes used to apply the drive signal and receive the bioimpedance signal.

Although illustrated and described throughout this disclosure as being a cardiac monitor, IMD 10 may be any of number of other implantable devices, including implantable hemodynamic monitors, blood chemistry monitors, pressure monitors, nerve monitors, muscle monitors, brain monitors, or the like. In any of these cases, IMD 10 may include additional sensors besides electrodes 14 and 16 to monitor desired physiological signals.

Figure 2:
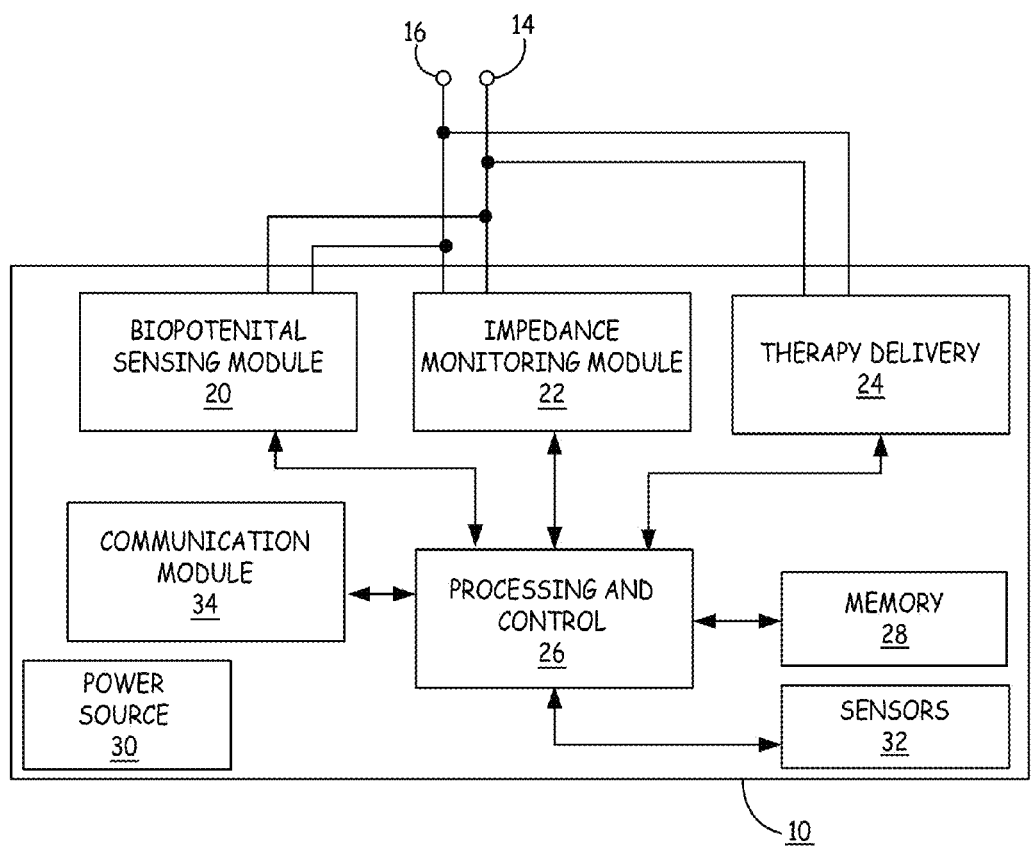
FIG. 2 is a functional block diagram of the IMD shown in FIG. 1.

FIG. 2 is a functional block diagram of IMD 10 shown in FIG. 1. IMD 10 includes a biopotential sensing module 20 and an impedance monitoring module 22 coupled to electrodes 14 and 16 for sensing biopotential signals and monitoring bioimpedance, respectively, within a patient.

IMD 10 may be embodied as a monitoring-only device without therapy delivery capabilities. In other examples, IMD 10 may include a therapy delivery module 24, which may be configured to generate electrical pulses for delivering therapeutic electrical stimulation, such as cardiac pacing, nerve stimulation, deep brain stimulation, or other neurostimulation. In such examples, therapy delivery module 24 is coupled to electrodes 14 and 16 for delivering electrical pulses to achieve a therapeutic benefit to the patient in addition to monitoring biopotential and bioimpedance signals of the patient. Sensing biopotential and bioimpedance signals during therapeutic stimulation pulse delivery may be temporarily blanked or interrupted to prevent saturation of sensing amplifiers during stimulation pulse delivery. Other examples of therapy delivery capabilities that may be included in therapy delivery module 24 include fluid delivery pumps for delivering a pharmacological agent, biological fluid or other therapeutic fluid.

Each of biopotential sensing module 20 and impedance monitoring module 22 may include an analog amplifier and/or filter for receiving an analog voltage signal from electrodes 14 and 16. Impedance monitoring module 22 includes a drive signal circuit and a measurement circuit for respectively applying a drive signal across electrodes 14 and 16 and measuring a resulting signal from which the impedance across electrodes 14 and 16 can be derived. For example, an alternating current (AC) drive signal may be applied across electrodes 14 and 16 and a bioimpedance signal is derived from a measured voltage signal. In some examples, the voltage signal may be used directly as an indication of impedance. Examples of devices that utilize impedance monitoring in which the techniques disclosed herein may be implemented are generally described in commonly-assigned U.S. Pat. No. 5,957,861 (Combs et al.), and pre-grant U.S. Publication No. 2010/0113962 (Hettrick, et al), each of which is incorporated herein by reference in its entirety.

As will be described herein, the analog voltage signals received from electrodes 14 and 16 are passed to analog-to-digital (A/D) converters included in each of biopotential sensing module 20, and impedance monitoring module 22 or in processing and control module 26. The A/D converters provide a sampled, digital signal of the biopotential signal received by biopotential sensing module 20 and the bioimpedance signal received by impedance monitoring module 22 to processing and control module 26 for further analysis according to a particular clinical application and/or storage in memory 28.

Processing and control module 26 and associated memory 28 control IMD functions and process signals received from electrodes 14 and 16 according to programmed signal analysis routines or algorithms. IMD 10 may include other optional sensors 32 for monitoring physiological signals, such as an activity sensor, pressure sensor, oxygen sensor, accelerometer, or other sensor used to monitor a patient.

As will be described in greater detail herein, processing and control module 26 controls the impedance monitoring module 22 to apply a drive signal synchronized to sampling intervals of the bioimpedance signal received by biopotential sensing module 20 to reduce feedthrough and DC aliasing of the drive signal delivered to electrodes 24 and 16 by impedance monitoring module 22 to the bioimpedance sensing module 20. Processing and control module 26 may control monitoring time intervals and sampling rates according to a particular clinical application. Processing and control module 26 may include state machines or other sequential logic circuitry to control device functions and need not be implemented exclusively as a microprocessor. Processor and control module 26, biopotential sensing module 20 and impedance monitoring module 22 may operate to acquire signal data and store processed or raw signal data in memory 28.

Communication module 34 includes an antenna and wireless transmitter to transmit electrical signal data, e.g. ECG signal data and impedance data, stored in memory 28 or received from processing and control module 26 in real time. Communication module 34 may be configured to transmit and receive communication signals via inductive coupling, electromagnetic coupling, tissue conductance, Near Field Communication (NFC), Radio Frequency Identification (RFID), BLUETOOTH®, WiFi, or other proprietary or non-proprietary wireless telemetry communication schemes.

A power source 30 provides power to each of the modules 20, 22, 24, 26, 34, memory 28 and sensors 32 as needed. Power source 30 may include one or more energy storage devices, such as one or more rechargeable or non-rechargeable batteries.

Modules 20, 22, 24, 26, 34, memory 28 and sensors 32 represent functionality included in IMD 10. Modules of the present disclosure may include any discrete and/or integrated electronic circuit components that implement analog and/or digital circuits capable of producing the functions attributed to the modules herein. For example, the modules may include analog circuits, e.g., pre-amplification circuits, filtering circuits, and/or other analog signal conditioning circuits. The modules may also include digital circuits, e.g., digital filters, combinational or sequential logic circuits, state machines, integrated circuits, a processor (shared, dedicated, or group) that executes one or more software or firmware programs, memory devices, or any other suitable components or combination thereof that provide the described functionality.

Memory 28 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), Flash memory, or any other memory device. Memory 28 may include non-transitory computer readable storage media storing instructions that, when executed by one or more processing circuits, cause the modules to perform various functions attributed to IMD 10. The storage media may include any computer-readable storage media with the sole exception being a transitory, propagating signal.

Depiction of different features as modules is intended to highlight different functional aspects and does not necessarily imply that such modules must be realized by separate hardware or software components. Rather, functionality associated with one or more modules may be performed by separate hardware, firmware and/or software components, or integrated within common hardware, firmware and/or software components.

Figure 3:
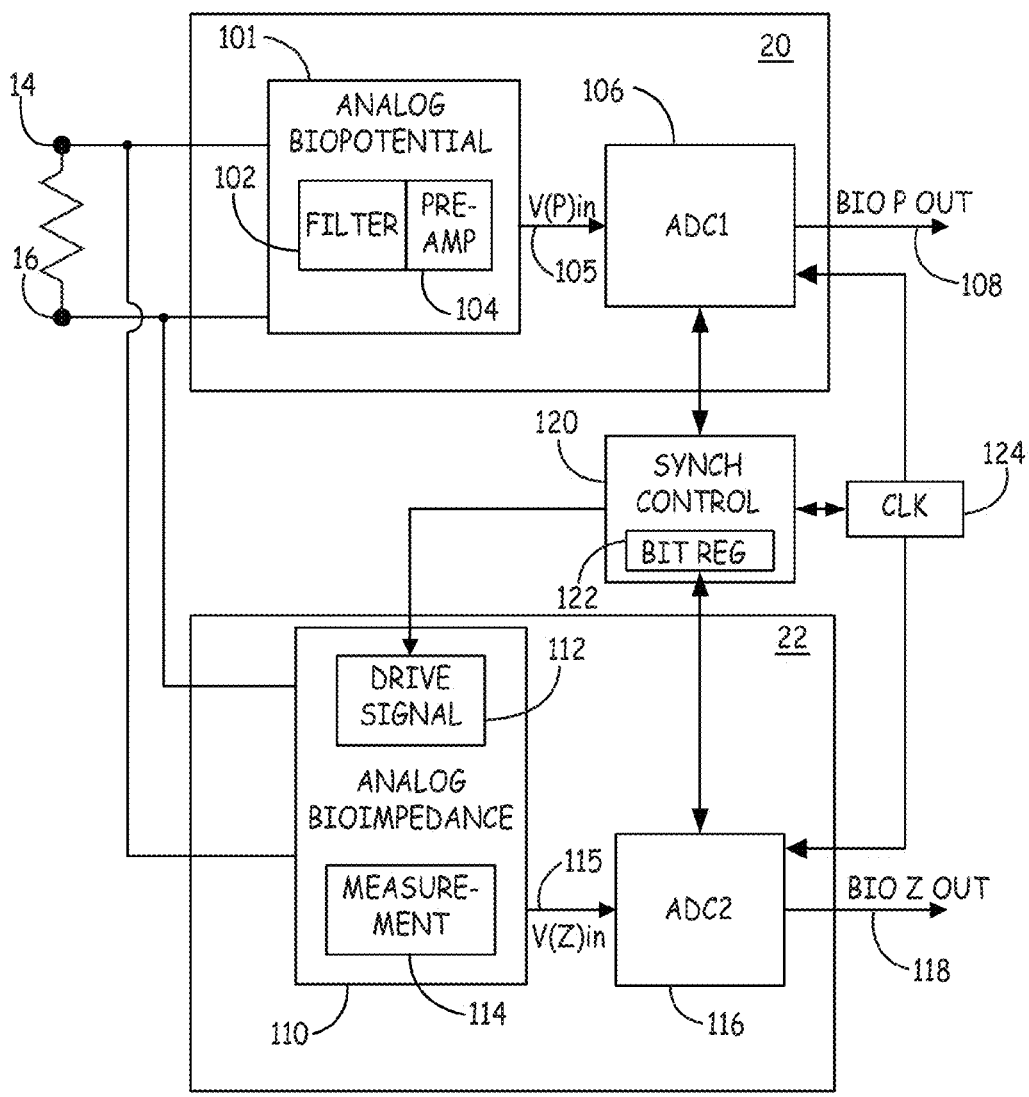
FIG. 3 is a functional block diagram depicting biopotential and bioimpedance signal acquisition functions of the IMD shown in FIG. 1.

FIG. 3 is a functional block diagram 100 of signal acquisition functions of IMD 10 that enable simultaneous biopotential and bioimpedance signal acquisition using a single electrode pair. Electrodes 14 and 16 are each coupled to biopotential sensing module 20 and bioimpedance monitoring module 22. Sensing module 20 and monitoring module 22 may be configured to receive differential signals from electrodes 14 and 16 or single-ended input signals may be received where one of the electrodes 14 or 16 is coupled to ground.

The biopotential sensing module 20 includes an analog sensing interface 101 for receiving signals from electrodes 14 and 16. Analog biopotential sensing interface 101 is shown to include an input filter 102 and analog pre-amplifier 104 and may include other analog circuitry for receiving a biopotential signal.

The output of the analog biopotential sensing interface 101 is provided as a biopotential input signal, V(P)in, 105 to an A/D converter (ADC1) 106. ADC1 106 generally includes a track and hold circuit for sampling V(P)in 105 and holding consecutive V(P)in sample points for digitization by ADC1 106. ADC1 may perform digital conversions using successive approximations, sigma delta conversions, timed ramp conversions, an integrating converter, or other conversion techniques or any combination thereof. A converted digital signal of V(P)in 105 is produced by ADC1 106 as digital output signal (BIO P OUT) 108.

In some examples, V(P)in 105 is oversampled by ADC1 106 and the oversampled signal points are filtered, e.g. by averaging over sampling cycles, to obtain a desired net sampling rate of the biopotential signal. For example, an ECG signal may be sampled at 16 kHz during a sampling cycle over which the 16 kHz signal samples are averaged to obtain a net sampling rate of 256 Hz. By averaging oversampled signal points, perturbations of V(P)in 105 due to application of the drive signal to electrodes 14 and 16 by impedance monitoring module 22 can be minimized as will be further described below. Digital filters, e.g. half-pass filters, low-pass filters, band-pass filters, averaging filters or other filtering methods may also be included in biopotential sensing module 20 for reducing drive signal artifact in the oversampled signal points accumulated from V(P)in 105.

Synchrony control module 120, which may be a component of processing and control module 26 shown in FIG. 2, may control the sampling rate of ADC1 106. The sampling rate may be set using clock signals generated by an integrated clock circuit 124.

The sampling rate of V(P)in 105 may be set according to a desired time resolution of the signal. For example, when electrodes 14 and 16 are positioned for sensing an ECG signal, an appropriate sampling rate may be 256 Hz, which may be obtained by oversampling the ECG signal and filtering or averaging the oversampled signal points as described above. Using the techniques disclosed herein, biopotential signal V(P)in 105 can be sampled continuously at the desired sampling rate independent of impedance measurements performed by the impedance monitoring module 22. In some examples, the biopotential signal V(P)in 105 is sampled continuously without interruption. In other examples, the biopotential signal is sampled continuously over intermittent or periodic monitoring intervals of time as controlled by synchrony control module 120 according to a monitoring protocol stored in IMD 10.

To illustrate, a biopotential signal may be monitored continuously and processing and control 26 may analyze the signal to detect clinical events. An episode of the continuously sampled biopotential signal is stored as an event episode in memory 28 in response to detecting the event. A sample recording and/or parameters derived from the biopotential signal may be stored.

Alternatively, the biopotential signal may be monitored during discontinuous monitoring intervals of time but sampled continuously within those monitoring intervals. Monitoring intervals may be scheduled times of day, periodic intervals, time intervals triggered in response to other physiological signals received by sensors 32 or in response to instructions received by communication module 34. During these discontinuous monitoring time intervals, biopotential signal recordings and/or parameters derived from the biopotential signal may be stored in memory 28. Whether the biopotential signal is monitored continuously over time or within discontinuous time intervals, the sampling of the biopotential signal occurs continuously at the designated sampling rate without interruption due to bioimpedance measurements. In particular, sampling of the biopotential signal received from electrodes 14 and 16 is not interrupted due to application of the drive signal to electrodes 14 and 16 by impedance monitoring module 22.

The impedance monitoring module 22 includes an analog impedance sensing interface 110. Interface 110 includes a drive signal circuit 112 and a measurement circuit 114. Drive signal circuit 112 has an AC signal source for applying a drive signal to electrodes 14 and 16. As will be described below, the AC drive signal timing, frequency and amplitude may be controlled by synchrony control module 120 and drive signal circuit 112 to minimize perturbation of the biopotential signal received by electrodes 14 and 16 when the drive signal is applied to the same electrodes 14 and 16 for monitoring a bioimpedance signal.

Drive signal circuit 112 may be coupled to electrodes 14 and 16 to provide a single-ended drive signal. Drive signal circuit 112 may include protection circuitry, such as an AC coupling capacitor. The coupling capacitor may be grounded in some examples between impedance monitoring intervals to discharge the capacitor. In other examples, the coupling capacitor is a floating capacitor that maintains a charge at a level between repetitive impedance monitoring intervals that reduces artifact on the biopotential signal received by biopotential sensing interface 101 at the onset of the drive signal.

Alternatively, drive signal circuit 112 may be coupled to electrodes 14 and 16 to provide a differential drive signal. In these instances, drive signal circuit 112 may include a pair of AC coupling capacitors, each coupled between the drive signal source included in circuit 112 and a respective electrode 14 and 16. The coupling capacitors may be pre-charged or adjusted to the same charge voltage prior to applying the drive signal to electrodes 14 and 16. By pre-charging the coupling capacitors to the same voltage prior to delivering a differential drive signal, onset and offset artifact in the biopotential signal caused by turning the drive signal ON and OFF can be reduced or eliminated as common mode signal that is rejected by the biopotential sensing interface 101.

Measurement circuit 114 receives the analog voltage signal response to the AC drive signal from electrodes 14 and 16, as either a single-ended input or differential input signal, and produces the analog voltage input signal (V(Z)in) 115 provided to ADC2 116. The measurement circuit 114 may include an analog filter and amplifier for filtering and amplifying the analog voltage signal received from electrodes 14 and 16. A chopper-stabilized instrumentation amplifier may be included in measurement circuit 114 as generally disclosed in commonly-assigned U.S. Pat. No. 7,622,988 (Denison, et al.), hereby incorporated herein by reference in its entirety. Measurement circuit 114 further includes a demodulator for demodulating the AC signal response recorded at electrodes 14 and 16 to a DC signal, V(Z)in 115. V(Z)in 115 is proportional to the bioimpedance across electrodes 14 and 16 and may be used directly to determine relative impedance changes or converted to a real and/or reactive component of the impedance signal using the drive current signal and measured voltage signal.

ADC2 116 receives the analog voltage input signal V(Z)in 115 and produces a digitized bioimpedance output signal (BIO Z OUT) 118. The A/D conversion operations performed by ADC2 116 for converting V(Z)in 115 to a digital output signal BIO Z OUT 118 may be analogous to the operation of ADC1 106 or may use different conversion techniques. For example, ADC2 116 generally uses a track and hold circuit for sampling the input signal V(Z)in 115 at any desired sampling rate and a comparator for comparing the V(Z)in signal sample to an internal digital-to-analog output signal to convert V(Z)in 115 to digital output signal BIO Z OUT 118. Conversion techniques may include those listed previously or any combination thereof. In one example, V(Z)in 115 is converted to BIO Z Out 118 in a two phase conversion process using successive approximations in the first phase and a sigma delta conversion in the second phase. Methods for controlling a drive signal as disclosed herein are not limited to use with any particular A/D conversion technique utilized by biopotential sensing module 20 or impedance monitoring module 22.

Synchrony control module 120 may provide timing control signals to ADC2 116, using clock signals from clock circuit 124, for setting the sampling rate of the bioimpedance signal V(Z)in 115. The sampling rate may vary between applications. For example, a bioimpedance signal used to monitor respiratory related conditions or changes may be sampled at a much lower sampling rate than a bioimpedance signal used to monitor cardiac related conditions or changes. The bioimpedance signal sampling rate may be equal to, greater than or less than a biopotential signal sampling rate and will be depend at least in part on the time resolution needed for the particular monitoring application.

In some examples, impedance monitoring module 22 operates in a manner that is dependent on the sampling cycle of the biopotential sensing module 20. Synchrony control module 120 provides control signals to drive signal source 112 based on the sampling cycle of ADC1 106 of the biopotential sensing module 20 and control bits set by bit register 122. The drive signal circuit 112 may be enabled to start and stop the drive signal applied to electrodes 14 and 16 in synchrony with edges of the sampling cycles of the biopotential signal. Synchrony control module 120 may include a state machine or other sequential logic circuitry for detecting a leading or trailing edge of biopotential signal sampling intervals produced by ADC1 106. As described in detail below, when an impedance monitoring interval is scheduled or triggered, synchrony control module 120 enables drive signal circuit 112 to synchronize delivery of the drive signal with the biopotential sample cycle.

Delivery of an AC drive signal to electrodes 14 and 16 can cause perturbation of the biopotential signal being sensed at the same electrodes 14 and 16. The drive signal may produce a DC offset and/or aliasing errors in the biopotential signal. For example, a significant DC offset of the biopotential signal received at the input of analog pre-amplifier 104 may occur when the drive signal is turned on and when it is turned off. Perturbations of the biopotential signal due to the impedance monitoring drive signal are minimized by synchronizing the onset and offset of the drive signal with biopotential signal sampling cycles during continuous sampling of the biopotential signal. The perturbation and drive signal-induced artifacts may be further minimized through adjustments to the AC drive signal amplitude and phase and selection of the frequency of the AC drive signal.

Figure 4:
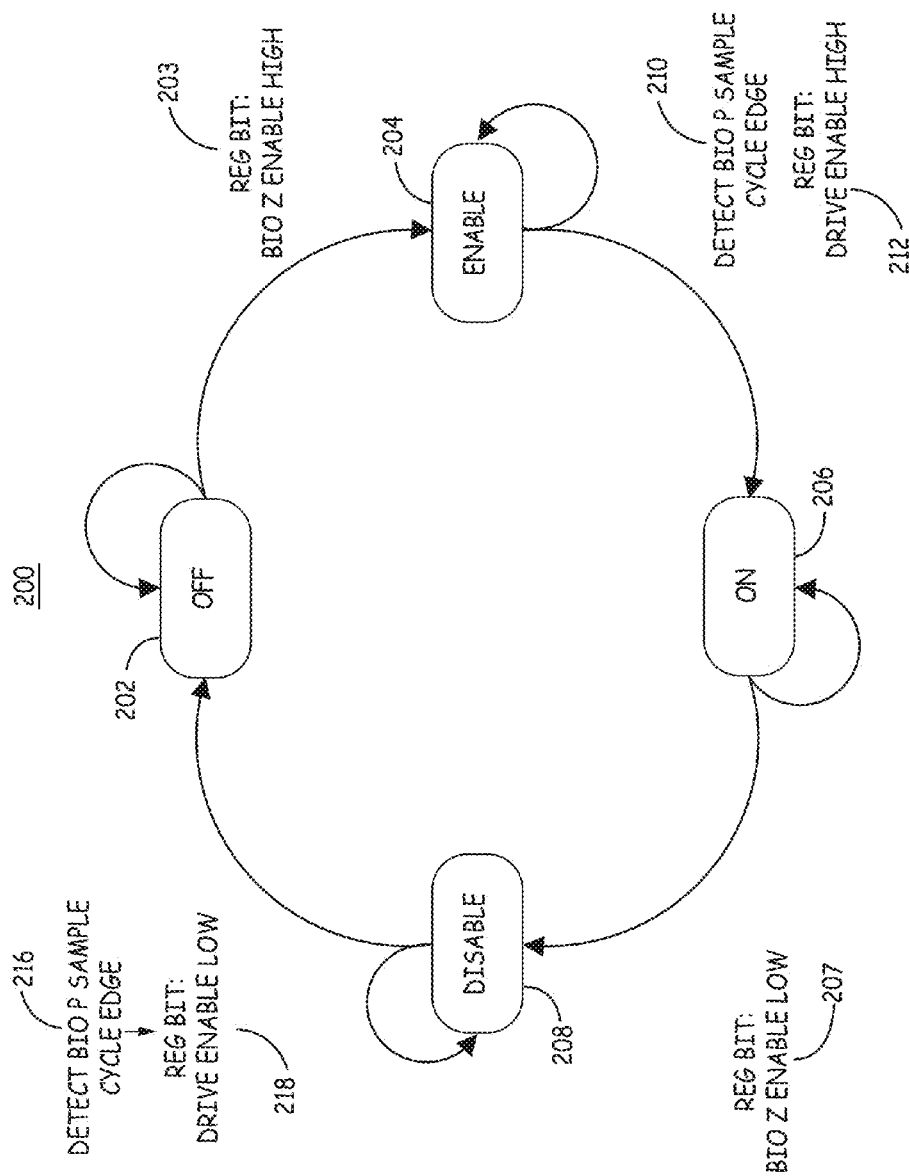
FIG. 4 is a conceptual diagram of operational states of an impedance monitoring module according to one embodiment.

FIG. 4 is a conceptual diagram 200 of operational states of the impedance monitoring module 22 according to one embodiment. Diagram 200 illustrates the states of impedance monitoring module 22 when controlled by a state machine in one embodiment. The states 202, 204, 206 and 208 may be controlled using other sequential logic circuitry or other processing and control circuitry in alternative embodiments. In an initial OFF state 202, the impedance monitoring module is disabled. The drive signal circuit may be powered down such that no drive signal is being delivered to electrodes 14 and 16.

The processing and control module 26 sets an impedance monitoring enable bit (BIO Z ENABLE) to a logical high value at 203 to enable the impedance monitoring module 22 to begin monitoring impedance. A logical high value of the BIO Z ENABLE signal indicates that impedance monitoring should begin. Application of the drive signal, however, will not begin immediately in response to the ENABLE signal. The drive signal onset will be synchronized to a leading or trailing edge of the sampling cycle of the biopotential signal. As such, the impedance monitoring module 22 transitions from the OFF state 202 to the ENABLE state 204 in response to a registration bit BIO Z ENABLE being set to logical high, but will remain in the ENABLE state 204, awaiting detection of a leading or trailing edge of the biopotential sampling cycle, before applying a drive signal and receiving a bioimpedance signal (e.g. a voltage signal in response to the AC drive signal). The ENABLE state 204 is an intermediate state in which the impedance monitoring module 22 is ready to begin monitoring, but is not yet delivering a drive signal and receiving a bioimpedance signal.

In the example shown, two conditions are required to transition from the ENABLE state 204 to the ON state 206. As indicated at 210, one condition is a detection of a leading edge of a sampling cycle of the biopotential signal. The sampling cycle leading edge is detected by synchrony control module 120, e.g. based on a clock signal received from clock circuit 124 or from the biopotential sensing module A/D converter ADC1 106.

In the enable state, the synchrony control module 120 sets a register bit DRIVE ENABLE signal to a logical high value after detecting an edge of the next biopotential signal sampling cycle as indicated at 212. The impedance monitoring module 22 transitions to the ON state 206. The impedance monitoring module 22 is fully operational in the ON state 206. The drive signal circuit 112 is powered up and applies the AC drive signal to electrodes 14 and 16. The voltage signal response to the drive signal is received by measurement circuit 114 from electrodes 14 and 16.

The impedance monitoring module 22 transitions from the ON state 206 to a DISABLE state 208 in response to the BIO Z ENABLE signal being set to logical low value as indicated at 207. Synchrony control module 120 may set the BIO Z ENABLE signal to a logical low value based on a scheduled or triggered ending time of an impedance monitoring time interval. In the DISABLE state 208, the impedance monitoring module 22 continues to apply the drive signal and acquire a bioimpedance signal until conditions are met for transitioning from the intermediate DISABLE state 208 to the OFF state 202. Impedance monitoring module 22 remains in the DISABLE state 208 at least until an edge of the next sampling cycle.

The synchrony control module 120 detects or recognizes a leading edge of the next sampling cycle of the biopotential signal as indicated at 216. In response to the leading edge of the next sampling cycle, the synchrony control module 120 sets the DRIVE ENABLE signal to logical low at 218. Upon setting the DRIVE ENABLE signal to logical low, the drive signal circuit 112 is terminated and the impedance monitoring module 22 returns to the OFF state 202.

The biopotential signal is sampled continuously throughout the impedance measurement module states 202, 204, 206 and 208 and the state transitions therebetween. If the drive signal is turned ON or OFF at a midway point in a biopotential sampling cycle, drive signal feedthrough appearing at the biopotential analog pre-amplifier will be present over a portion of the biopotential signal sampling cycle. This feedthrough noise may result in aberrancies in the digitized biopotential signal output. By turning the drive signal on and off synchronously with an edge of the biopotential sampling cycles, artifact due to starting and stopping the drive signal is present only at the onset of a sampling cycle. By oversampling the biopotential signal and averaging or filtering the oversampled points to obtain the desired sampling rate, the onset and offset artifact, occurring only at an edge of the sampling cycles, and any drive signal feedthrough noise will be minimized and trend towards a net zero artifact.

Figure 5A:
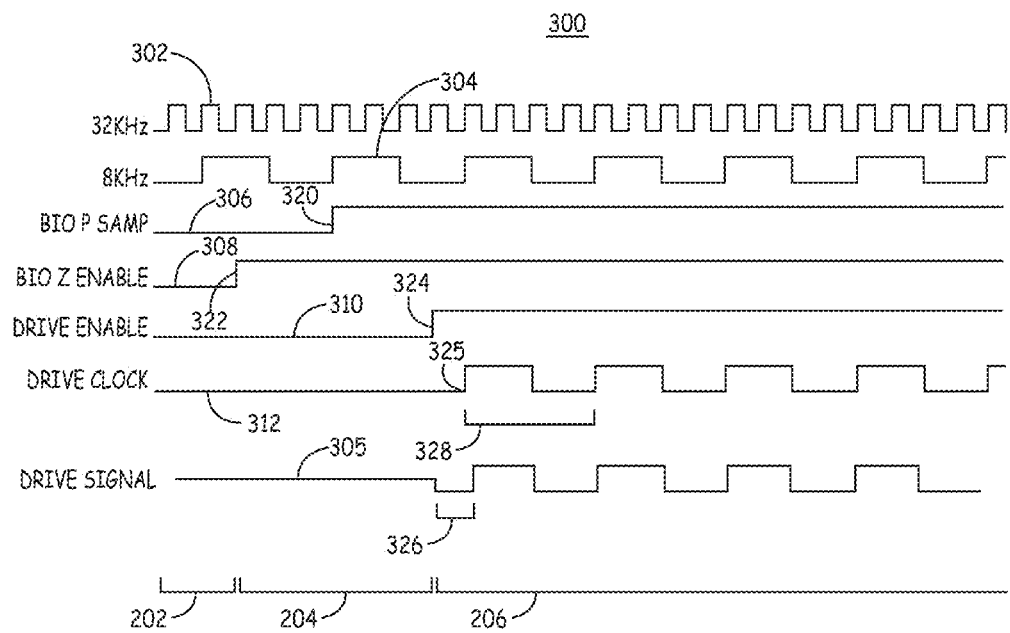
FIGS. 5A, 5B and 5C are timing diagrams of various signals used to control an impedance monitoring module according to different illustrative examples.
Figure 5B:
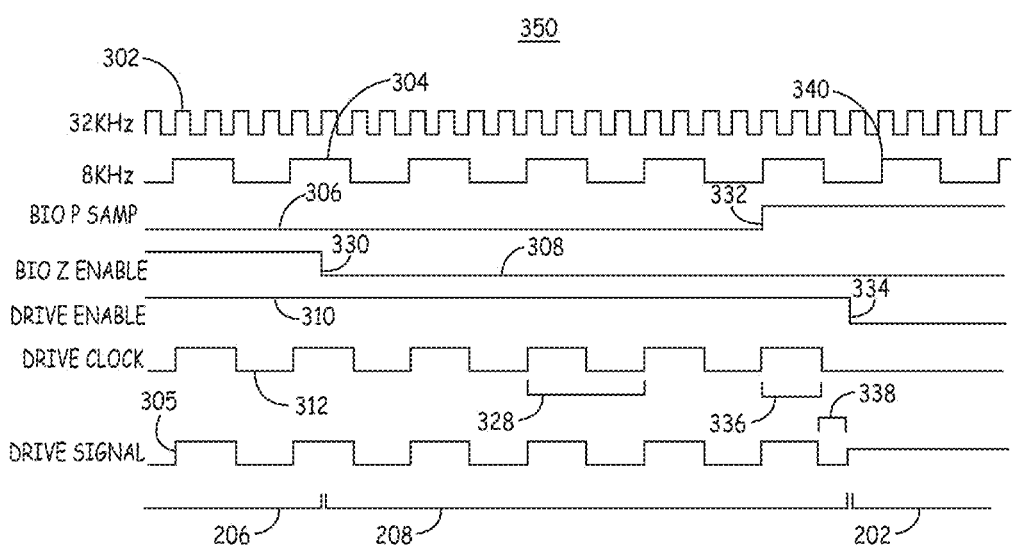

FIGS. 5A and 5B are timing diagrams of various signals used to control the impedance monitoring module 22 according to one illustrative example. In FIG. 5A and FIG. 5B, a 32 KHz clock signal 302 and an 8 KHz clock signal 304 are shown as free-running integrated circuit clock signals that provide timing signals for other control signals. A bioimpedance drive clock signal 312 is also shown running in phase with the 8 KHz clock signal 304, though other drive signal clock frequencies could be used. It is recognized that the particular frequencies of the clock signals 302 and 304 described in conjunction with the example shown in FIGS. 5A and 5B are illustrative and should not be construed as limiting. Clock signals used to control biopotential sampling frequencies and bioimpedance drive signals and sampling frequencies may vary between embodiments and may be used with frequency dividers, multipliers or other circuitry for obtaining desired signal frequencies for controlling the various functions of the biopotential sensing module 20 and impedance monitoring module 22.

Logic signals BIO P SAMP 306, BIO Z ENABLE 308 and DRIVE ENABLE 310, are also shown in FIGS. 5A and 5B. Logic signals 306, 308 and 310 are bit signals set in bit register 122 if synchrony control logic 120. The clock signals 302, 304, and 312 along with the bit signals 306, 308 and 310 are used for controlling and state transitions of the impedance monitoring module as described below.

FIG. 5A is a timing diagram 300 of signals used to control a start-up sequence performed to enable the impedance monitoring module to transition from an OFF state 202 to an ON state 206 in which the drive signal 305 is delivered synchronized to a sampling cycle of the biopotential signal and a bioimpedance signal is acquired. In particular, the drive signal 305 is enabled or turned on in synchrony with a leading edge 320 of a sampling cycle of the biopotential signal as controlled by BIO P SAMP 306.

In this example, the biopotential signal is acquired at a sampling rate of 256 Hz by oversampling the biopotential signal at a sampling frequency of 16 KHz (controlled by the 32 KHz clock in the implementation shown) to accumulate oversampled signal points. The oversampled signal points are then filtered or averaged over sampling cycles corresponding to the 256 Hz sampling rate to obtain the desired 256 Hz sampled biopotential signal. The leading edge 320 of BIO P SAMP 306 is therefore the leading edge of a sampling cycle of the biopotential signal, during which the biopotential signal may be oversampled to accumulate signal sample points that are averaged or filtered to obtain the desired biopotential signal sampling rate in some embodiments.

The impedance monitoring module is initially in the OFF state 202, as described previously. In the OFF state 202, no drive signal is applied to electrodes 14 and 16 and no bioimpedance signal is being acquired. The synchrony control module 120 sets the BIO Z ENABLE signal 308 to a logical high value at 322. This BIO Z ENABLE signal 308 may be set high according to a monitoring protocol implemented in IMD 10, e.g., in response to a scheduled time of day, a periodic monitoring interval, a sensor-based trigger, or a user command.

In response to the BIO Z ENABLE signal 308 being set high at 322, the impedance monitoring module transitions from the OFF state 202 to the intermediate ENABLE state 204, wherein the impedance monitoring module is ready but waiting for the next leading edge 320 of the biopotential sampling cycle in order to synchronize the onset of the AC drive signal 305 to the start of a biopotential sampling cycle. In response to the next leading edge 320 after the BIO Z ENABLE signal is set high at 322, the synchrony control module sets a DRIVE ENABLE signal 310 to a logical high value at 324.

The DRIVE ENABLE signal 310 is set to logical high at 324 on a leading edge of the 32 KHz clock cycle, prior to the next 8 KHz clock cycle. The impedance monitoring module transitions from the intermediate ENABLE state 204 to the ON state 206 in response to the DRIVE ENABLE signal 310 being set high. The impedance monitoring module 22 applies the drive signal 305 to the electrodes 14 and 16 and begins sampling the bioimpedance signal at a desired sampling rate, which may be the same or different than the biopotential sampling rate.

The drive signal clock 312 controls the drive signal frequency, at 8 KHz in this example. The drive signal clock 312 has a clock period that is in phase with the 8 KHz clock 304. The synchrony control module 120 sets that DRIVE ENABLE signal 310 high at 324 such that the onset of the drive signal 305 shifted in phase relative to the origin 325 of the next drive clock period 328. In this example, the drive signal 305 will be delivered for a one-quarter cycle 326 of the drive clock period 328, followed by full cycles of the drive clock period 328 defining the AC drive signal frequency. The drive signal is started with a phase difference of one-quarter of a full clock period from the origin 325 of the drive signal clock period 328.

By starting the drive signal with a one-quarter cycle 326 of drive clock period 328, and averaging oversampled signal points of the biopotential signal, a drive signal artifact appearing on the biopotential signal at the beginning of the sampling cycle starting with leading edge 320 is minimized. The impedance monitoring module remains in the ON state 206 as long as the BIO Z ENABLE signal 308 remains at the logical high value.

FIG. 5B is a timing diagram 350 of signals used to control a stopping sequence performed to disable the impedance monitoring module by transitioning the impedance monitoring module from the ON state 206 to an OFF state 202, in which the drive signal is off, i.e. no longer delivered to the electrodes 14 and 16, and a bioimpedance signal is not acquired. At the end of a bioimpedance monitoring interval, the synchrony control module sets the BIO Z ENABLE signal 308 to a logical low value at 330.

The BIO Z ENABLE signal 308 may be switched to low based on an implemented monitoring protocol, e.g. based on a time of day, the expiration of a periodic or predetermined monitoring time interval, a change in another sensor signal, or upon user command. The impedance monitoring module transitions from the ON state 206 to the intermediate DISABLE state 208 in response to the BIO Z ENABLE signal 308 being set low at 330. The impedance monitoring module awaits a leading edge 332 of the BIO P SAMP signal 306 during the DISABLE state 208.

In response to the next leading edge 332 of the next biopotential sampling cycle, the synchrony control module 120 sets the DRIVE ENABLE signal 310 to a logical low at 334. The impedance monitoring module transitions from the intermediate DISABLE state 208 to the OFF state 202. The drive signal 305, which has been cycling in phase with the drive clock signal 312, is thereby disabled, and bioimpedance signal acquisition is terminated at 334.

In this example, the DRIVE ENABLE signal 310 is controlled by the synchrony control to be switched low after the leading edge 332 of the biopotential sampling cycle and following a one half cycle 336 of the drive signal clock period 328. The drive signal clock 312, running in phase with the 8 KHz clock, completes at least one half cycle 336 following the leading edge 332 of the biopotential sampling cycle. The synchrony control module 120 switches the DRIVE ENABLE signal 310 to low after the half cycle 336 but before the next 8 KHz clock cycle 340 as controlled by the 32 KHz clock signal 302. This timing results in a final quarter-cycle 338 of the drive signal 305 at the termination of the drive signal 305, synchronized to the beginning of the biopotential sampling cycle starting at leading edge 332.

In this way, the onset and offset artifact of the drive signal present in the biopotential signal is limited to a quarter-cycle or other portion less than the drive signal clock period 328 at the leading or trailing edge of a biopotential signal sampling period. This partial cycle of the drive signal at its onset and offset the artifact reduces the artifact produced in the digital biopotential output signal (BIO P OUT 108 in FIG. 3).

In alternative examples, the onset and offset of the drive signal 305 may be synchronized to trailing edges of the biopotential sampling cycles or a combination of leading and trailing edges. Synchronization of the drive signal onset and offset with a leading or trailing edge of the biopotential sampling cycle can include a delay or lag of one-half cycle of the drive signal clock period or more while the impedance monitoring module is in an intermediate ENABLE state 204 or intermediate DISABLE state 206 while awaiting an edge of the biopotential sampling cycle before the transitioning to the ON or OFF states 206 and 202, respectively. A lag in a state transition may also include a lag following the edge detection of a biopotential sampling cycle based on a desired phase shift of the drive signal relative to the drive signal clock period.

Techniques for synchronizing the drive signal onset and/or offset may, therefore, include techniques for grading the onset and/or offset of the drive signal for reducing the drive-signal induced artifact produced in the biopotential signal. As described in the foregoing, techniques for grading the drive signal onset and offset may include shifting the phase of the drive signal relative to the origin of a drive signal clock period. Shifting the phase of the drive signal onset may be achieved by enabling the drive signal a portion of a drive signal clock period earlier than a full clock period origin. Shifting the phase of the drive signal offset may be achieved by disabling the drive signal a portion of a drive signal clock period later than the end of a full clock period. One technique for shifting the phase of the drive signal onset and offset relative to the drive signal clock period origin is illustrated by the onset and offset quarter-cycles 326 and 328 in FIGS. 5A and 5B. It is recognized that other methods may be conceived for implementing a phase shift at the onset of the drive signal 305 relative to the origin 325 of a drive signal clock period 328 and for extending the drive signal 305 a portion of a drive signal clock period after a full clock period to achieve a partial drive signal cycle at offset.

Figure 5C:
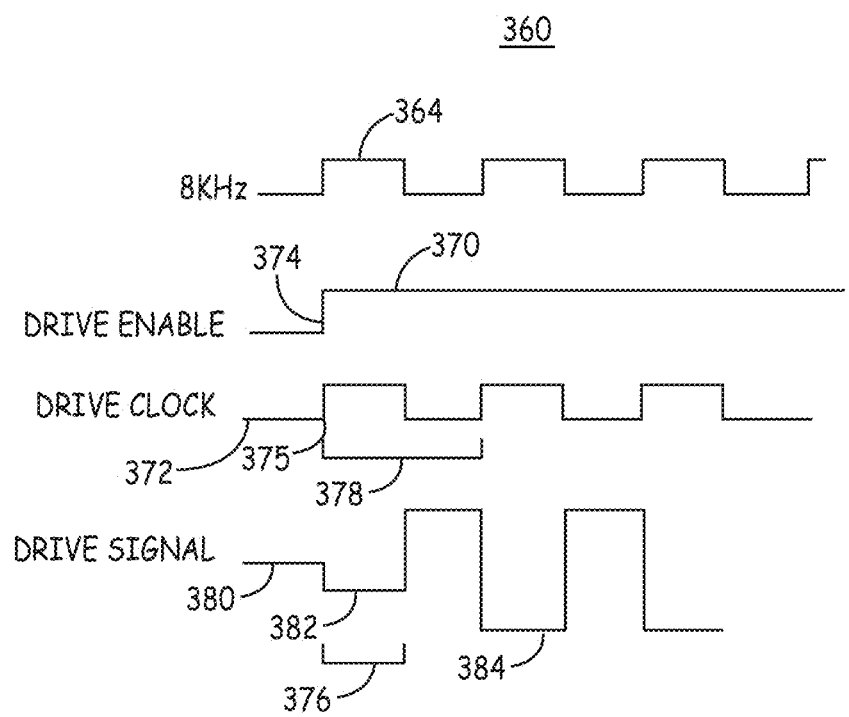

FIG. 5C is a timing diagram 360 depicting the use of a reduced drive signal current amplitude 382 at the onset of the drive signal 380. Techniques for grading a drive signal onset and/or offset to reduce biopotential signal artifact due to the drive signal may additionally or alternatively include applying a reduced drive signal amplitude during the first and/or last drive signal cycles or portions thereof.

In the example of FIG. 5C, the DRIVE ENABLE signal 370 is set high at 374 after an ENABLE signal is set high and an edge of the biopotential sampling signal is detected (as described above). In this case, however, the ENABLE signal 370 is set high at an origin 375 of the drive clock period 378. The drive signal 380 is enabled or turned ON in phase with the period 378 of drive clock signal 372. Drive signal 380 is not shifted in phase relative to drive clock period 378 in this example as opposed to the quarter-cycle phase shift shown in FIG. 5A.

In this embodiment, the DRIVE ENABLE signal 370 is set high in synchrony with the 8 KHz clock signal 364 (rather than the 32 KHz clock signal as shown in FIG. 5A) such that the onset cycle 376 of drive signal 380 is a full one-half cycle of clock period 378. The drive signal source, however, is controlled to deliver the drive signal 380 during the onset cycle 376 with a lower current amplitude 382 than the full drive signal current amplitude 384 that is delivered on subsequent drive signal cycles. For example, the drive signal current amplitude 382 may be half the full drive signal current amplitude 384 for the first one-half cycle 376 at the onset of drive signal 380.

Similarly, the drive signal 380 may be delivered with a current amplitude less than the full drive signal current amplitude 384 at the drive signal offset, e.g., for the last one-half cycle of the drive signal 380 delivered in phase with drive clock period 378 at the termination of drive signal 380. A reduced current drive signal may be delivered for a full cycle, half cycle, quarter cycle or other portion of the drive signal clock period 378 at the onset and/or offset of the drive signal to provide a graded drive signal onset and/or offset.

In alternative embodiments, a graded drive signal onset and/or offset may include a ramped drive signal amplitude rather than a discretely adjusted drive signal amplitude as shown in FIG. 5C. The artifact on the biopotential signal is influenced by the slope of the ramped drive signal amplitude. The higher the slope, the greater the signal artifact amplitude may be. A slope of the ramped drive signal, controlled by a starting amplitude and the portion of the drive clock period over which the ramped drive signal amplitude is applied before reaching the full drive signal amplitude, may be selected to minimize the artifact produced on the biopotential signal.

In one example, a single-ended drive signal is applied to one of electrodes 14 or 16 through a coupling capacitor. The drive signal current amplitude is ramped over at least a portion of the onset cycle, which may be in phase or out of phase with the drive clock period and may be a full cycle or a portion of a full cycle of the drive clock period. The slope of the ramped current amplitude may be low, i.e. a relatively slow ramping up of the drive signal current amplitude, such that it is rejected by the filter 102 of the biopotential sensing interface 101 (shown in FIG. 3).

Accordingly, techniques for reducing the onset and offset artifact induced by the drive signal in the biopotential signal received by the biopotential sensing module 20 include shifting a phase of the drive signal and/or reducing an amplitude of the drive signal during an initial and final drive signal clock period or portion thereof. By shifting the phase and/or reducing the onset and/or offset current of the drive signal using a discrete step change in amplitude or a ramped amplitude, a graded drive signal is provided to reduce the associated artifact produced on the biopotential signal being monitored from a common pair of electrodes.

Figure 6:
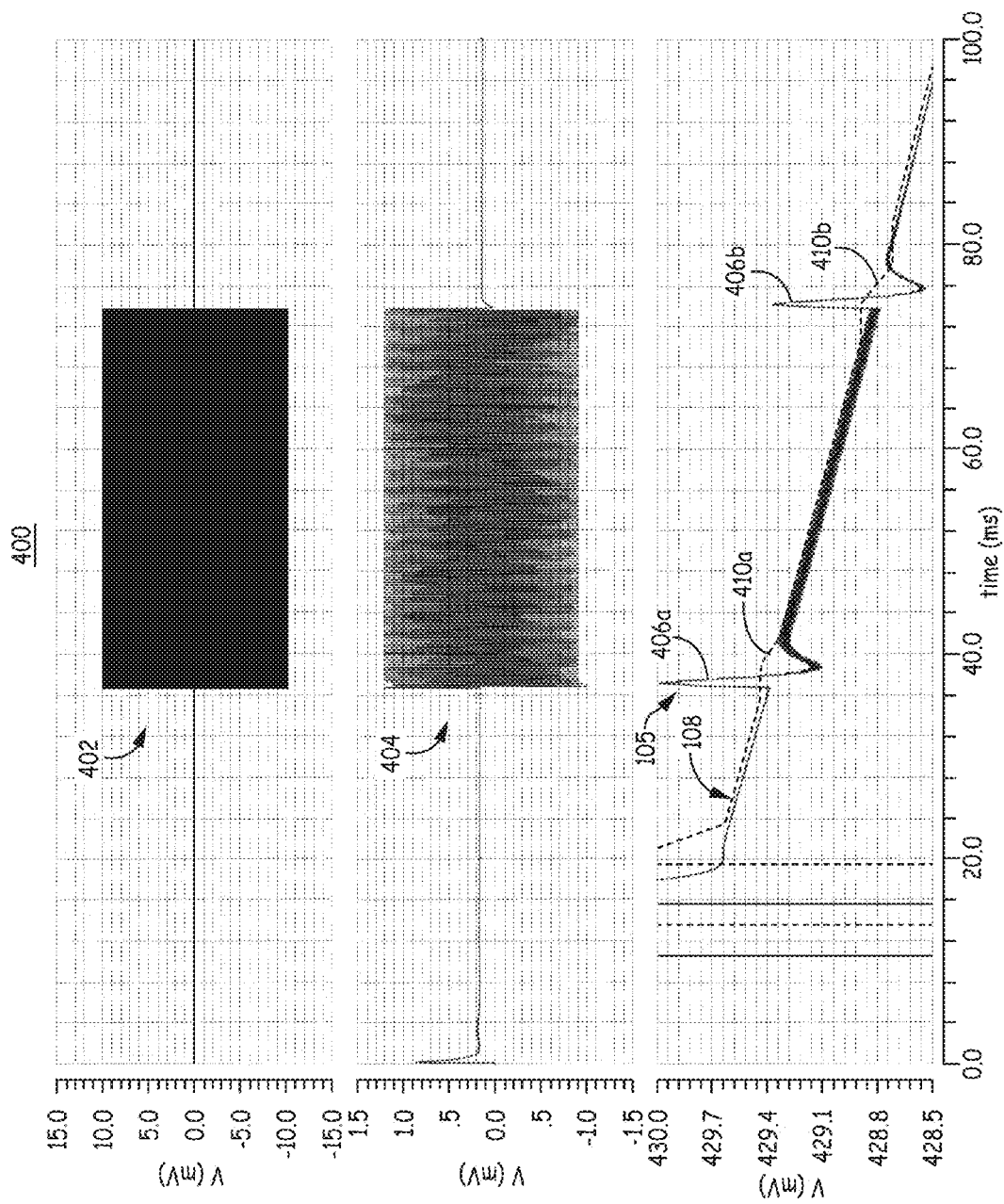
FIG. 6 is an example plot depicting a drive signal applied by an impedance monitoring module to a pair of implanted electrodes and the resulting artifact received by a biopotential sensing module from the same pair of electrodes.

FIG. 6 is an example plot 400 depicting a drive signal 402 applied by the impedance monitoring module to the electrodes 14 and 16 and the resulting artifact received by the biopotential sensing module. The drive signal 402 applied to the electrodes 14 and 16 by impedance monitoring module is shown as an 8 KHz, 20 mV peak-to-peak square wave. Drive signal feedthrough noise 404 appears as an approximately 2.3 mV peak-to-peak signal at the input of the analog sensing interface 101 of the biopotential sensing module 20. The output of the analog sensing interface 101, V(P)in 105, is provided as input to the ADC1 106 of the biopotential sensing module 20. The drive signal feedthrough noise 404 is attenuated by the analog sensing interface 101 to an approximately 62 µV peak-to-peak signal in V(P)in 105, received at the input of ADC1 106.

V(P)in 105 also includes onset and offset artifacts 406a and 406b occurring upon enabling the drive signal 402 and disabling the drive signal 402, respectively. By synchronizing the onset of drive signal 402 and the offset of drive signal 402 with the leading edge of biopotential sampling cycles as described herein, and averaging oversampled biopotential signal points to obtain a desired biopotential signal sampling rate, the feedthrough noise and the onset and offset drive signal artifacts 410a and 410b in the output signal 108 of ADC1 106 are minimized. The remaining drive signal onset and offset artifacts 410a and 410b in output signal BIO P OUT 108 are reduced to be substantially within a baseline noise level of the biopotential signal-to-noise ratio. The feedthrough noise 404 tends to zero in the ADC1 output signal 108 due to averaging the oversampled biopotential signal points. Any effect of feedthrough noise 404 that remains in the output signal 108 is distributed evenly through the biopotential sampling cycle since the drive signal is enabled near the beginning of the sampling cycle and will not be disabled until a leading edge of the next sampling cycle. This feedthrough noise is therefore substantially removed by averaging. The frequency of the drive signal 402 is shown as 8 KHz in this example.

The feedthrough noise amplitude and presence of DC aliasing is influenced by the drive signal frequency used. In order to reduce interference on the biopotential signal caused by the drive signal, a drive signal frequency can be selected that results in less DC aliasing and a lower feedthrough noise. Accordingly, the drive signal frequency selected is a frequency that produces less interference of the input signal V(P)in 105 to ADC1 106 than other available drive signal frequencies.

Figure 7:
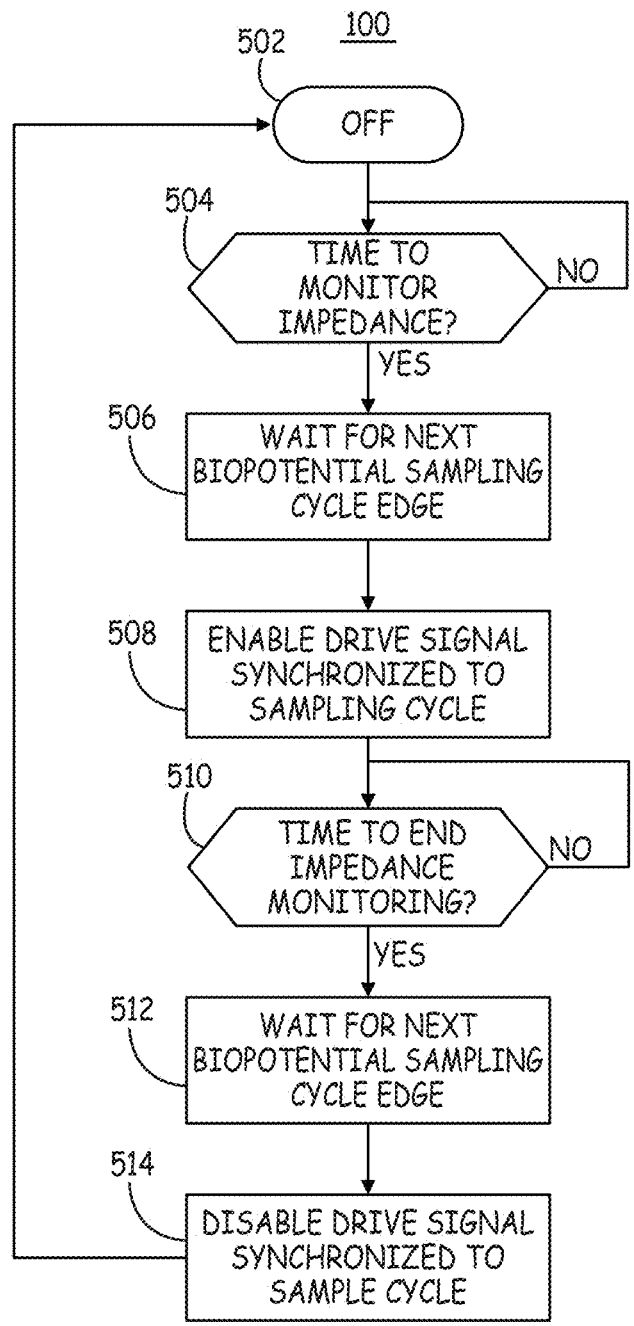
FIG. 7 is a flow chart of a method for controlling an impedance monitoring module according to one embodiment.

FIG. 7 is a flow chart 500 of a method for controlling an impedance monitoring module according to one embodiment. As described herein, IMD 10 includes processing and control circuitry configured to control an impedance monitoring module to deliver a drive signal to and receive a bioimpedance signal from the same pair of electrodes being used to acquire a biopotential signal being sampled continuously over a monitoring time interval. During the biopotential monitoring time interval, the biopotential signal is sampled at a desired sampling rate, which may be achieved by oversampling the biopotential signal and filtering, e.g. by averaging, the oversampled signal points over sampling cycles corresponding to the desired sampling rate.

At any time during the continuous sampling of the biopotential signal, a signal indicating that it is time to acquire a bioimpedance signal may be produced by the processing and control module. The impedance monitoring module is initially OFF at block 502. In response to the processing and control module determining that it is time to start monitoring bioimpedance at block 504, the impedance monitoring module transitions into an ENABLE state and waits for an edge of the next biopotential sampling cycle at block 506.

Upon detecting an edge of the next biopotential sampling cycle, the drive signal is enabled, synchronized to the sampling cycle at block 508. For example, the drive signal may be enabled at the leading edge of the biopotential sampling cycle. Synchronization of the drive signal to a sampling cycle of the biopotential signal can include a delay until the drive signal is actually turned on based on a desired phase of the drive signal relative to a drive signal clock period. As described above, the drive signal may be turned on after waiting for a clock period to complete after the leading edge of the sampling cycle so that a partial cycle, e.g. a quarter cycle, of the drive signal frequency cycle is delivered at the beginning of the biopotential sampling cycle. By delivering a partial cycle of an AC drive signal, the net drive signal onset artifact may be reduced in the digitized biopotential output signal. Additionally or alternatively, the AC drive signal may be delivered during at least a portion of an onset cycle at a current amplitude less than the full drive signal current amplitude. In this way, a graded drive signal onset is synchronized to an edge of the biopotential sampling cycle.

The impedance monitoring module remains in the ON state until a signal is received indicating it is time to stop impedance monitoring as determined at block 510. The impedance monitoring module continues to deliver the drive signal and acquire the bioimpedance signal while waiting for the next biopotential sampling cycle edge at block 512. The drive signal is disabled in synchrony with the next sampling cycle edge at block 514.

Synchronization of the drive signal offset may include delivering a graded drive signal offset by using a partial offset cycle that is a portion of the drive signal clock cycle period and/or a reduced drive signal current amplitude. As such, synchronization of the drive signal offset with a biopotential sampling cycle edge may include a lag time or delay to allow a drive clock period to complete followed by a portion of a drive clock period for a final offset cycle. For example, the synchrony control module may wait for a full cycle of the drive signal frequency to complete after the biopotential sampling cycle edge then terminate the drive signal after a partial cycle, e.g. one-quarter of the drive signal clock period. Additionally or alternatively, the drive signal current may be reduced from a full drive signal current during a final drive signal cycle, which may be a whole drive signal clock period or portion thereof.

After disabling the drive signal, the impedance monitoring module returns to the OFF state 502 to await the next bioimpedance monitoring interval. Meanwhile, the biopotential signal may continue to be sampled using the same electrode pair without interruption and independently of the impedance monitoring time interval and bioimpedance sampling rate.

Thus, an implantable medical device and associated methods for acquiring biopotential and bioimpedance signals using a single common electrode pair have generally been presented in the foregoing description with reference to specific embodiments. Various examples described herein may be combined in any combination other than the illustrative examples presented herein and some aspects may be added or omitted without departing from the scope of the disclosure. Methods for synchronizing a bioimpedance drive signal with a biopotential sampling cycle may include steps performed in a different order or combination than the illustrative examples shown and described herein. It is appreciated that various modifications to the referenced embodiments may be made without departing from the scope of the disclosure as set forth in the following claims.

The invention claimed is:

1. An implantable medical device, comprising:
   a pair of electrodes;
   a biopotential sensing module coupled to the pair of electrodes and configured to acquire a biopotential signal present at the pair of electrodes at a first sampling rate;
   an impedance monitoring module comprising a drive signal circuit coupled to the pair of electrodes and configured to deliver a drive signal from the drive signal circuit to the pair of electrodes and acquire a bioimpedance signal across the pair of electrodes at a second sampling rate;
   a control module configured to control the first sampling rate of the biopotential signal and to control the impedance monitoring module to transition from an off state to an on state during a period of continuous sampling of the biopotential signal at the first sampling rate by enabling an onset of the drive signal that is synchronized to at least one of a leading edge and a trailing edge of a sampling cycle of the first sampling rate.

2. The device of claim 1, wherein the impedance monitoring module comprises an alternating current source for delivering the drive signal,
   the control module further configured to control the impedance monitoring module to deliver the drive signal at a first drive signal frequency that produces less interference on a biopotential signal received by the biopotential sensing module than a second drive signal frequency different than the first drive signal frequency.

3. The device of claim 1, wherein the control module is configured to enable the drive signal in response to a first edge of a sampling cycle corresponding to the first sampling rate and disable the drive signal in response to a next edge of the sampling cycle corresponding to the first sampling rate.

4. The device of claim 1, wherein the biopotential sensing module is configured to oversample the biopotential signal at a third sampling rate greater than the first sampling rate to acquire oversampled signal points and filter the oversampled signal points over a sampling cycle corresponding to the first sampling rate to obtain sampled signal points at the first sampling rate.

5. The device of claim 4, wherein the control module is configured to synchronize the drive signal by enabling the drive signal in response to a first edge of the sampling cycle and disabling the drive signal in response to a next edge of the sampling cycle.

6. The device of claim 1, wherein the control module is configured to control transitions of the impedance monitoring module between a first state wherein the drive signal is disabled and a second state wherein the drive signal is enabled,
   wherein controlling a transition from the first state to the second state comprises controlling an intermediate transition from the first state to a first intermediate state in response to an impedance monitoring enable signal followed by a next transition from the first intermediate state to the second state in response to a first edge of a sampling cycle corresponding to the first sampling rate, and
   controlling a transition from the second state to the first state comprises controlling an intermediate transition from the second state to a second intermediate state in response to an impedance monitoring disable signal followed by a next transition from the second intermediate state to the first state in response to a second edge of the sampling cycle corresponding to the first sampling rate.

7. The device of claim 1, wherein the biopotential sensing module is configured to sample the biopotential signal continuously at the first sampling frequency over a monitoring interval independent of the second sampling frequency during the monitoring interval.

8. The device of claim 1, wherein the control module is configured to synchronize the drive signal by enabling and disabling the drive signal in response to an edge of a sampling cycle corresponding to the first sampling rate,
   the impedance monitoring module configured to deliver an alternating current drive signal having a drive signal period in response to the control module enabling the drive signal; and
   the control module further configured to control the impedance monitoring module to deliver the alternating current drive signal with at least one of an onset cycle less than one half of the drive signal period and an offset cycle less than one half of the drive signal period.

9. The device of claim 1, wherein the drive signal has a first amplitude and a second amplitude less than the first amplitude,
the control module being further configured to control the impedance monitoring module to deliver the drive signal for at least one of an onset portion and an offset portion at the second amplitude.

10. The device of claim 1, wherein the control module is further configured to control the impedance monitoring module to start the drive signal shifted in phase from a phase origin of a drive signal clock period.

11. A method, comprising:
acquiring a biopotential signal by a sensing module coupled to at a pair of electrodes at a first sampling rate;
delivering a drive signal to the pair of electrodes;
sensing a bioimpedance signal at a second sampling rate in response to the drive signal across the pair of electrodes by an impedance monitoring module coupled to the pair of electrodes; and
controlling the drive signal in synchrony with the first sampling rate to transition from an off state to an on state during a period of continuous sampling of the biopotential signal at the first sampling rate by enabling an onset of the drive signal that is synchronized to at least one of a leading edge and a trailing edge of a sampling cycle of the first sampling rate.

12. The method of claim 11, further comprising:
delivering an alternating current drive signal; and
delivering the alternating current drive signal at a first drive signal frequency that produces less interference on a biopotential signal than a second drive signal frequency different than the first drive signal frequency.

13. The method of claim 11, further comprising enabling the drive signal in response to a first edge of a sampling cycle corresponding to the first sampling rate and disabling the drive signal in response to a next edge of the sampling cycle corresponding to the first sampling rate.

14. The method of claim 11, further comprising:
oversampling the biopotential signal at a third sampling rate greater than the first sampling rate to acquire oversampled signal points; and
filtering the oversampled signal points over a sampling cycle corresponding to the first sampling rate to obtain sampled signal points at the first sampling rate.

15. The method of claim 14, further comprising synchronizing the drive signal by enabling the drive signal in response to a first edge of the sampling cycle and disabling the drive signal in response to a next edge of the sampling cycle.

16. The method of claim 11, further comprising controlling transitions of the impedance monitoring module between a first state wherein the drive signal is disabled and a second state wherein the drive signal is enabled,
wherein controlling a transition from the first state to the second state comprises controlling an intermediate transition from the first state to a first intermediate state in response to an impedance monitoring enable signal followed by a next transition from the first intermediate state to the second state in response to a first edge of a sampling cycle corresponding to the first sampling rate, and
controlling a transition from the second state to the first state comprises controlling an intermediate transition from the second state to a second intermediate state in response to an impedance monitoring disable signal followed by a next transition from the second intermediate state to the first state in response to a second edge of the sampling cycle corresponding to the first sampling rate.

17. The method of claim 11, further comprising sampling the biopotential signal continuously at the first sampling frequency over a monitoring interval independent of the second sampling frequency during the monitoring interval.

18. The method of claim 11, further comprising synchronizing the drive signal by enabling and disabling the drive signal in response to an edge of a sampling cycle corresponding to the first sampling rate,
delivering an alternating current drive signal having a drive signal period in response to enabling the drive signal; and
controlling the alternating current drive signal to have at least one of an onset cycle less than one half of the drive signal period and an offset cycle less than one half of the drive signal period.

19. The method of claim 11, further comprising:
delivering the drive signal at a first amplitude; and
delivering at least one of an onset portion and an offset portion of the drive signal at a second amplitude less than the first amplitude.

20. The method of claim 11, further comprising shifting the drive signal in phase from a phase origin of a drive signal clock period.

21. An implantable medical device, comprising:
sensing means for acquiring a biopotential signal at a pair of electrodes at a first sampling rate;
sensing means for acquiring a bioimpedance signal across the pair of electrodes at a second sampling rate; and
control means for controlling transition of the sensing means for acquiring the bioimpedance signal from an off state to an on state during a period of continuous sampling of the biopotential signal at the first sampling rate by enabling an onset of a drive signal that is synchronized to at least one of a leading edge and a trailing edge of a sampling cycle of the first sampling rate, the drive signal delivered to the pair of electrodes for acquiring the bioimpedance signal.

22. A non-transitory, computer-readable storage medium storing a set of instructions, which when executed by a control module of an implantable medical device causes the device to:
control a sensing module configured to acquire a biopotential signal from a pair of electrodes at a first sampling rate;
control an impedance monitoring module configured to acquire a bioimpedance signal across the pair of electrodes at a second sampling rate; and
control the impedance monitoring module to transition from an off state to an on state during a period of continuous sampling of the biopotential signal at the first sampling rate by enabling an onset of a drive signal that is synchronized to at least one of a leading edge and a trailing edge of a sampling cycle of the first sampling rate, the drive signal delivered to the pair of electrodes for acquiring the bioimpedance signal.

23. The device of claim 1, further comprising a wireless transmitter configured to transmit biopotential signal data and bioimpedance signal data to an external device for monitoring a physiological condition of a patient.

24. The device of claim 1, further comprising a clock circuit providing a clock signal to the control module for setting the first sampling rate and the second sampling rate,
wherein enabling an onset of the drive signal circuit synchronized to at least one of a leading edge and a trailing edge of a sampling cycle of the first sampling rate comprises starting the onset of the drive signal shifted in phase by less than one-half cycle of a clock period of the second sampling rate.

25. The device of claim 1, further comprising determining a physiological condition of a patient based on the biopotential signal data and the bioimpedance signal data.

26. The device of claim 1, further comprising a therapy delivery module configured to deliver therapy based on the physiological condition.

* * * * *